United States Patent [19]
Burgoyne et al.

[11] Patent Number: 6,054,120
[45] Date of Patent: Apr. 25, 2000

[54] SUNSCREEN APPLICATOR SYSTEM

[76] Inventors: Bradley C. Burgoyne; Gail E. Burgoyne, both of 6696 45th Ave. SW., Pequot Lakes, Minn. 56472

[21] Appl. No.: 09/415,583

[22] Filed: Oct. 8, 1999

[51] Int. Cl.[7] ............................. A61K 7/42; A61K 7/44; A61K 7/00

[52] U.S. Cl. ........................... 424/59; 424/60; 424/400; 424/401

[58] Field of Search ................................. 424/59, 60, 400, 424/401

[56] References Cited

U.S. PATENT DOCUMENTS

| | | | |
|---|---|---|---|
| 3,103,682 | 9/1963 | Markle | 424/401 |
| 4,559,225 | 12/1985 | Fourman | 424/59 |
| 4,759,652 | 7/1988 | Ulrich | 401/196 |
| 4,817,790 | 4/1989 | Porat et al. | 206/205 |
| 5,017,365 | 5/1991 | Niedbala | 424/59 |
| 5,368,581 | 11/1994 | Smith et al. | 604/290 |
| 5,487,932 | 1/1996 | Dunshee | 428/68 |
| 5,972,360 | 10/1999 | Braun | 424/59 |

Primary Examiner—Shelley A. Dodson
Attorney, Agent, or Firm—Michael S. Neustel

[57] ABSTRACT

A sunscreen applicator system for conveniently storing and dispensing various types of sunscreen lotion within a convenient compact structure. The inventive device includes at least one packaging, a towel sealed within the packaging containing sunscreen lotion, a container for storing at least one packaging, and a storage case for receiving a storing a plurality of containers. Each of the containers and packaging contains an SPF indicia indicating the SPF level of the sunscreen lotion within the packaging. A diverse selection of SPF levels are provided by all of the containers for allowing the user to select from. If the user desires, an individual packaging may be positioned within their wallet, purse or other storage area for later use during the day. The storage case includes a plurality of sides, a floor, an upper opening and a cover pivotally attached to one of the sides. The storage case preferably includes a partition member above the floor of the storage case for creating a waste reservoir wherein a disposal slot extends into said storage case connecting to the waste reservoir for allowing an individual to insert waste material into the waste reservoir.

20 Claims, 3 Drawing Sheets

SUNSCREEN APPLICATOR SYSTEM

BACKGROUND OF THE INVENTION

1. Field of the Invention

The present invention relates generally to sunscreen applications and more specifically it relates to a sunscreen applicator system for conveniently storing and dispensing various types of sunscreen lotion within a convenient compact structure.

Individuals who are exposed to the sun require the usage of sunscreen. Depending upon the individual's skin type and weather conditions, the sun protection factor (SPF) is generally adjusted thereby allowing a desirable tan to be achieved with reduced skin damage. Hence, there is a need for a sunscreen applicator system that is capable of dispensing various types of sunscreen lotion and oil.

2. Description of the Prior Art

Sunscreen lotions and oils have been in use for years. Typically, the sunscreen lotions and oils are stored within a bottle-like container with a dispensing nozzle or removable cover thereby allowing the individual to dispense the sunscreen lotions or oils upon their skin.

Unfortunately, conventional sunscreen applicator devices do not provide a complete and even coverage of the user's body thereby leaving some skin areas overexposed and some underexposed to the sun. Another problem with conventional sunscreen applicator devices is that the user is generally limited to carrying one container thereby limiting their selection of sunscreens to only one SPF level.

Examples of attempted solutions to these problems include U.S. Pat. No. 5,017,365 to Niedbala; U.S. Pat. No. 5,368,581 to Smith et al.; U.S. Pat. No. 3,103,682 to M. L. Markle; U.S. Pat. No. 4,759,652 to Ulrich; U.S. Pat. No. 4,817,790 to Porat et al.; U.S. Pat. No. 5,487,932 to Dunshee; U.S. Pat. No. 4,559,225 to Fourman which are all illustrative of such prior art.

Niedbala (U.S. Pat. No. 5,017,365) discloses a sunscreen composition and applicator system. Niedbala teaches fibrous sheets impregnated with the compositions which can be packaged in vapor-and moisture impermeable containers for storage.

Smith et al. (U.S. Pat. No. 5,368,581) discloses a method of using a packaging system with folded applicator pads for topical drug delivery. Smith et al teaches a method for applying a plurality of dermatological agents to the skin from a single dispensing system.

M. L. Markle (U.S. Pat. No. 3,103,682) discloses a lotion applicator. M. L. Markle teaches an applicator having an extendable handle so that various parts of the body may be conveniently treated.

While these devices may be suitable for the particular purpose to which they address, they are not as suitable for conveniently storing and dispensing various types of sunscreen lotion within a convenient compact structure. Conventional sunscreen dispensing systems are inconvenient to utilize and do not allow the user to utilize various types of sunscreen solution from a single compact structure.

In these respects, the sunscreen applicator system according to the present invention substantially departs from the conventional concepts and designs of the prior art, and in so doing provides an apparatus primarily developed for the purpose of conveniently storing and dispensing various types of sunscreen lotion within a convenient compact structure.

SUMMARY OF THE INVENTION

In view of the foregoing disadvantages inherent in the known types of sunscreen applicators now present in the prior art, the present invention provides a new sunscreen applicator system construction wherein the same can be utilized for conveniently storing and dispensing various types of sunscreen lotion within a convenient compact structure.

The general purpose of the present invention, which will be described subsequently in greater detail, is to provide a new sunscreen applicator system that has many of the advantages of the sunscreen applicators mentioned heretofore and many novel features that result in a new sunscreen applicator system which is not anticipated, rendered obvious, suggested, or even implied by any of the prior art sunscreen applicators, either alone or in any combination thereof.

To attain this, the present invention generally comprises at least one packaging, a towel sealed within the packaging containing sunscreen lotion, a container for storing at least one packaging, and a storage case for receiving a storing a plurality of containers. Each of the containers and packaging contains an SPF indicia indicating the SPF level of the sunscreen lotion within the packaging. A diverse selection of SPF levels are provided by all of the containers for allowing the user to select from. If the user desires, an individual packaging may be positioned within their wallet, purse or other storage area for later use during the day. The storage case includes a plurality of sides, a floor, an upper opening and a cover pivotally attached to one of the sides.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a sunscreen applicator system that will overcome the shortcomings of the prior art devices.

Another object is to provide a sunscreen applicator system that provides various types of sunscreen lotions and oils within a compact dispensing structure.

An additional object is to provide a sunscreen applicator system that is easily transported and is self-contained.

A further object is to provide a sunscreen applicator system that provides for a convenient sunscreen dispensing system.

Another object is to provide a sunscreen applicator system that increases the coverage and evenness of coverage upon the skin of the user.

An additional object is to provide a sunscreen applicator system that utilizes convenient and disposable clothes or lotion packets for dispensing lotion.

A further object is to provide a sunscreen applicator system that includes various SPF levels of sunscreen lotion.

An additional object is to provide a sunscreen applicator system that decreases the amount of time required to apply sunscreen to the user's skin.

Another object is to provide a sunscreen applicator system that allows individual packets to be carried with the individual user for use when the original protective layers are reduced due to water exposure or other events.

A further object is to provide a sunscreen applicator system that may be conveniently stored within a wallet, purse or other small enclosed area.

An additional object is to provide a sunscreen applicator system that eliminates the need for bulky, heavy and awkward bottle containers.

A further object is to provide a sunscreen applicator system that does not have build-up or other debris attached to the container after extended usage as with conventional containers.

Another object is to provide a sunscreen applicator system that has a built in disposal portion for receiving refuse thereby maintaining a cleaner environment.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DESCRIPTION OF THE PREFERRED EMBODIMENT

Figure 1:
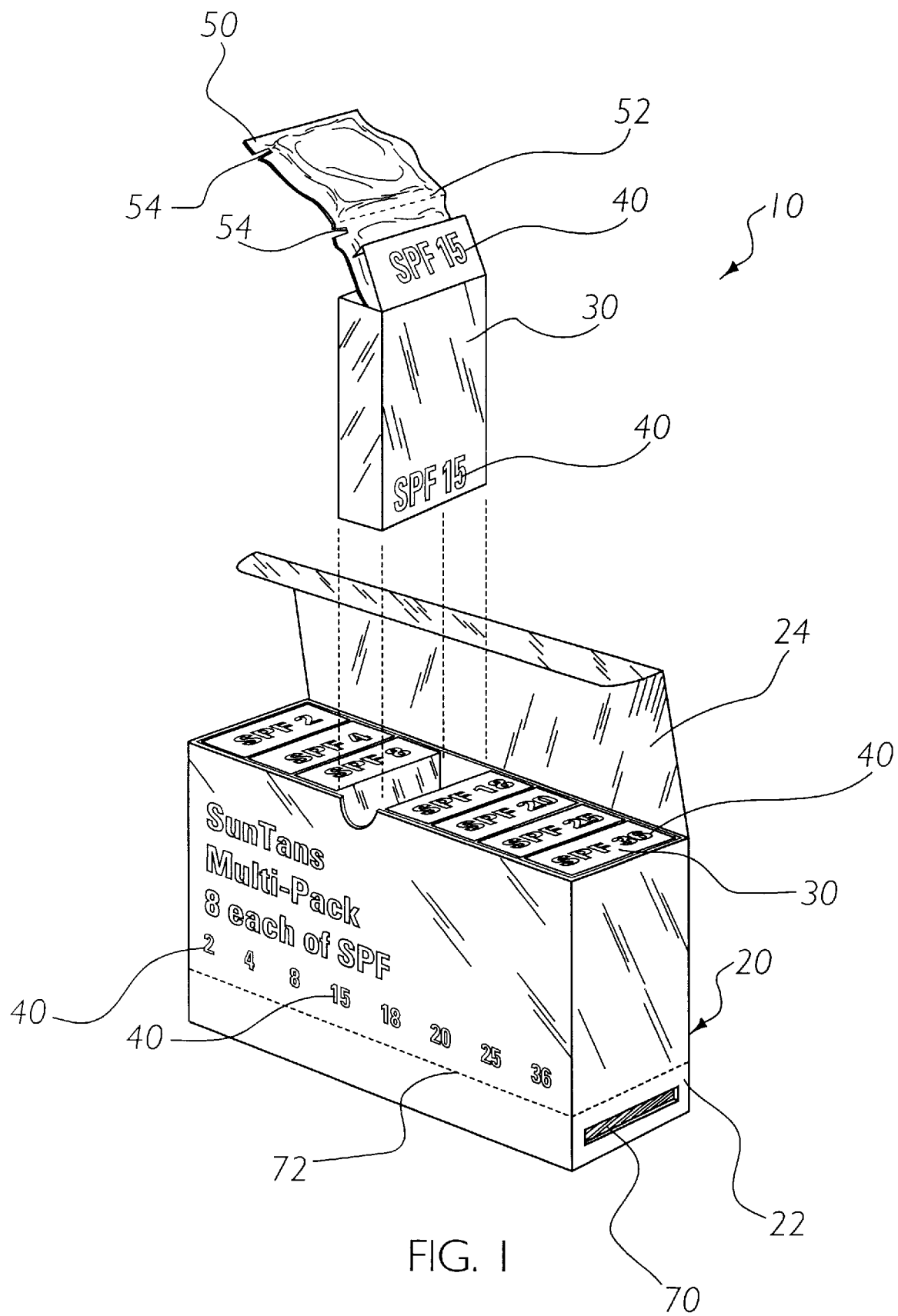
FIG. 1 is an exploded upper perspective view of the present invention.
Figure 2:
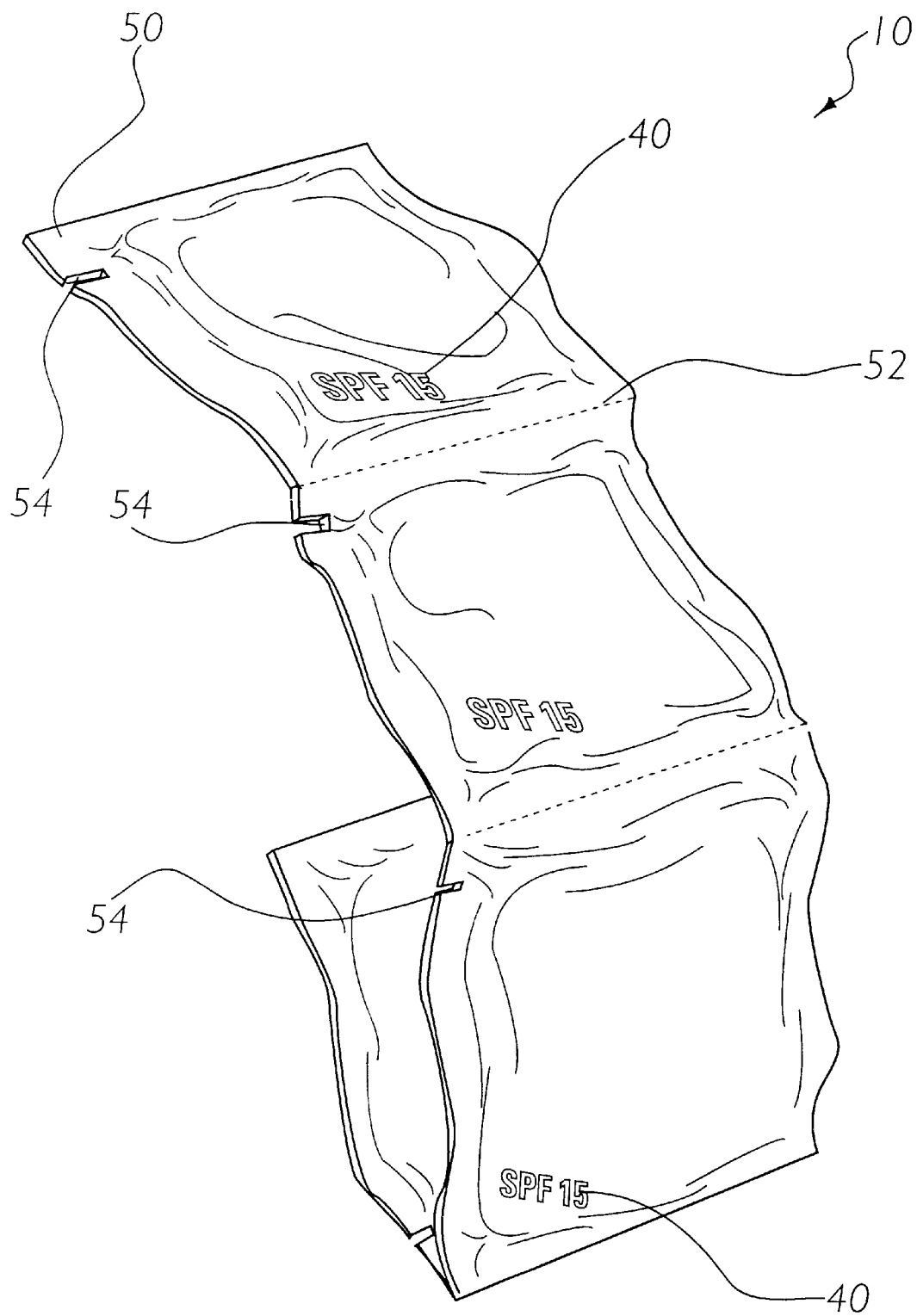
FIG. 2 is an upper perspective view of the packaging showing the perforations.
Figure 3:
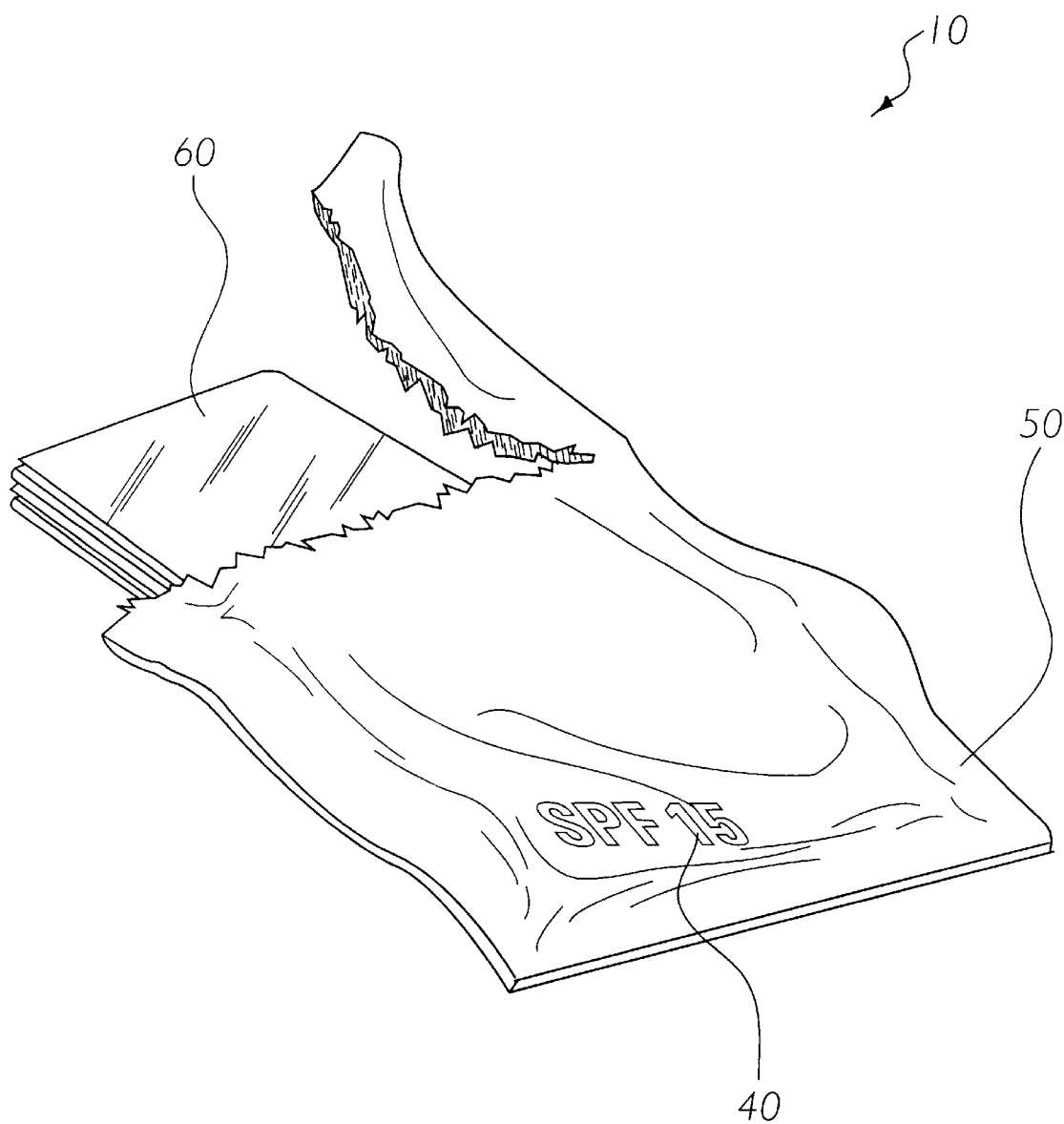
FIG. 3 is an upper perspective view of a single packaging member torn from the tear notch showing the towel within.

Turning now descriptively to the drawings, in which similar reference characters denote similar elements throughout the several view, FIGS. 1 through 3 illustrate a sunscreen applicator system 10, which comprises at least one packaging 50, a towel 60 sealed within the packaging 50 containing sunscreen lotion, a container for storing at least one packaging 50, and a storage case 20 for receiving a storing a plurality of containers 30. Each of the containers 30 and packaging 50 contains an SPF indicia 40 indicating the SPF level of the sunscreen lotion within the packaging 50. A diverse selection of SPF levels are provided by all of the containers 30 for allowing the user to select from. If the user desires, an individual packaging 50 may be positioned within their wallet, purse or other storage area for later use during the day. The storage case 20 includes a plurality of sides 22, a floor, an upper opening and a cover 24 pivotally attached to one of the sides 22.

As best shown in FIG. 2 of the drawings, the packaging 50 preferably has a plurality of compartments that store the towel 60 along with the sunscreen lotion. Each of the compartments is preferably separated by perforations 52 thereby allowing the compartments to be separated without exposing the interior portion of the compartments. The packaging 50 is constructed of an impermeable opaque material for protecting the towel 60 and sunscreen lotion within.

As shown in FIG. 2 of the drawings, the packaging 50 includes a plurality of tear notches 54 that correspond to an end of each compartment. The tear notches 54 allow an individual to tear the packaging 50 thereby exposing the towel 60 and lotion inside of the compartment as shown in FIG. 3 of the drawings. As further shown in FIGS. 2 and 3 of the drawings, the packaging 50 further includes an SPF indicia 40 which indicates the SPF rating of the sunscreen lotion within the compartment and within the towel 60.

As shown in FIG. 3 of the drawings, a towel 60 is positioned within the compartment of the packaging 50. Each towel 60 is constructed of a cloth or fibrous material that absorbs and dispenses sunscreen lotion. The towel 60 may be constructed of any well-known shape and structure.

As shown in FIG. 1 of the drawings, a plurality of containers 30 receiving the packaging 50 based upon the level of SPF. As shown in FIG. 1 of the drawings, each of the containers 30 includes a corresponding SPF indicia 40 to indicate the SPF level of the sunscreen within.

As further shown in FIG. 1 of the drawings, a storage case 20 is provided for storing the plurality of containers 30. The storage case 20 includes a plurality of sides 22, a floor, an upper opening and a pivotally attached cover 24. The interior cavity of the storage case 20 is capable of storing a plurality of containers 30. As shown in FIG. 1 of the drawings, the exterior surface of the storage case 20 includes an SPF indicia 40 for indicating which level of SPF is in each of the containers 30.

As shown in FIG. 1 of the drawings, the storage case 20 includes a partition member 72 that acts as a false floor within the storage case 20 for supporting the containers 30 a finite distance above the floor of the storage case 20. A disposal slot 70 extends through one of the walls of the storage case 20 thereby allowing refuse and the packaging 50 to be inserted into after the packaging 50 is opened thereby preventing waste material from entering the environment.

In an alternative embodiment, each of the compartments within the packaging 50 is only filled with sunscreen lotion without a towel 60 within. To use the alternative embodiment, the user simply tears the packaging 50 and squeezes the compartment thereby forcing the sunscreen lotion outwardly through the tear.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A sunscreen applicator system, comprising:
   a packaging having at least one compartment within;
   a towel within said compartment; and
   an amount of sunscreen within said compartment.

2. The sunscreen applicator system of claim 1, wherein said sunscreen is also impregnated within said towel.

3. The sunscreen applicator system of claim 2, wherein said packaging includes at least one row of perforations that separate a plurality of said compartments.

4. The sunscreen applicator system of claim 3, wherein said packaging is impermeable and opaque.

5. The sunscreen applicator system of claim 4, wherein said packaging includes at least one tear notch for allowing easy opening by a user.

6. The sunscreen applicator system of claim 5, wherein said packaging includes an SPF indicia that corresponds to an SPF rating of said sunscreen.

7. The sunscreen applicator system of claim 6, wherein said plurality of said compartments are rectangular shaped.

8. A sunscreen applicator system, comprising:
   a packaging having at least one compartment within; and
   an amount of sunscreen within said compartment.

9. The sunscreen applicator system of claim 8, wherein said packaging includes at least one row of perforations that separate a plurality of said compartments.

10. The sunscreen applicator system of claim 9, wherein said packaging is impermeable and opaque.

11. The sunscreen applicator system of claim 10, wherein said packaging includes at least one tear notch for allowing easy opening by a user.

12. The sunscreen applicator system of claim 11, wherein said packaging includes an SPF indicia that corresponds to an SPF rating of said sunscreen.

13. The sunscreen applicator system of claim 12, wherein said plurality of said compartments are rectangular shaped.

14. A sunscreen applicator system, comprising:
   a storage case having a plurality of sides, a floor, and a cover pivotally attached thereto;
   a partition member secured within said storage case a finite distance above said floor for creating a refuse reservoir;
   a slot within one of said plurality of sides extending into said refuse reservoir for allowing insertion of refuse into said refuse reservoir;
   a plurality of containers positionable within said storage case, wherein said plurality of containers include an SPF indicia indicating a specific SPF level;
   at least one packaging having at least one compartment within; and
   an amount of sunscreen within said compartment.

15. The sunscreen applicator system of claim 14, including a towel positioned within said at least one compartment.

16. The sunscreen applicator system of claim 15, wherein said packaging includes at least one row of perforations that separate a plurality of said compartments.

17. The sunscreen applicator system of claim 16, wherein said packaging is impermeable and opaque.

18. The sunscreen applicator system of claim 17, wherein said packaging includes at least one tear notch for allowing easy opening by a user.

19. The sunscreen applicator system of claim 18, wherein said packaging and said containers include an SPF indicia that corresponds to an SPF rating of said sunscreen.

20. The sunscreen applicator system of claim 19, wherein said plurality of said compartments are rectangular shaped.

* * * * *